(12) United States Patent
Shin (10) Patent No.: US 9,205,228 B2
(45) Date of Patent: Dec. 8, 2015

(54) CATHETER OPERATING STRUCTURE

(75) Inventor: Kyong Min Shin, Seoul (KR)

(73) Assignees: TAEWOONG MEDICAL CO., LTD., Gyeonggi-do (KR); Kyong Min Shin, Seoul (KR)

(*) Notice: Subject to any disclaimer, the term of this patent is extended or adjusted under 35 U.S.C. 154(b) by 202 days.

(21) Appl. No.: 13/990,682

(22) PCT Filed: Nov. 14, 2011

(86) PCT No.: PCT/KR2011/008654
§ 371 (c)(1),
(2), (4) Date: May 30, 2013

(87) PCT Pub. No.: WO2012/081833
PCT Pub. Date: Jun. 21, 2012

(65) Prior Publication Data
US 2013/0253423 A1    Sep. 26, 2013

(30) Foreign Application Priority Data
Dec. 14, 2010    (KR) .................. 10-2010-0127621

(51) Int. Cl.
A61F 2/06    (2013.01)
A61M 25/01    (2006.01)
A61F 2/95    (2013.01)

(52) U.S. Cl.
CPC .............. *A61M 25/0113* (2013.01); *A61F 2/95* (2013.01); *A61F 2002/9517* (2013.01); *A61M 25/0136* (2013.01)

(58) Field of Classification Search
None
See application file for complete search history.

(56) References Cited

U.S. PATENT DOCUMENTS

| | | | | |
|---|---|---|---|---|
| 4,445,757 A * | 5/1984 | Enomoto et al. | ............... | 359/696 |
| 5,306,248 A | 4/1994 | Barrington | | |
| 5,906,619 A * | 5/1999 | Olson et al. | ................... | 606/108 |
| 6,866,669 B2 * | 3/2005 | Buzzard et al. | ............... | 606/108 |
| 2005/0027305 A1 * | 2/2005 | Shiu et al. | .................... | 623/1.11 |
| 2005/0159726 A1 | 7/2005 | Evans et al. | | |
| 2006/0282150 A1 * | 12/2006 | Olson et al. | .................. | 623/1.11 |
| 2010/0030255 A1 * | 2/2010 | Berra et al. | ................... | 606/200 |

FOREIGN PATENT DOCUMENTS

JP    64-046450    2/1989
KR    1020030044486    6/2003

* cited by examiner

*Primary Examiner* — Tuan V Nguyen
(74) *Attorney, Agent, or Firm* — IP & T Group LLP (57) ABSTRACT

Provided is a catheter operating structure in which a medical device such as a stent is rotated to move forward or backward without being repeatedly pushed or pulled when inserted into the lumen of a human body, so that a surgical position can be precisely adjusted by the forward or backward movement. A rotary member includes a spiral shaft formed on a handle so as to be inserted into a tubular body. A movable member includes a female spiral end that is formed at one end thereof and is spirally coupled with the spiral shaft. An injection member moving member moves together with the movable member. When the spiral shaft is rotated by rotation of the handle with the spiral shaft spirally coupled to the female spiral end, the movable member moves forward or backward without being rotated due to the injection member moving member.

7 Claims, 11 Drawing Sheets

CATHETER OPERATING STRUCTURE

This application is a national stage application of PCT/KR2011/008654 filed on Nov. 14, 2011, which claims priority of Korean patent application number 10-2010-0127621 filed on Dec. 14, 2010. The disclosure of each of the foregoing applications is incorporated herein by reference in its entirety.

TECHNICAL FIELD

The present invention relates, in general, to a catheter operating structure and, more particularly, to a catheter operating structure in which a medical device such as a stent is rotated to move forward or backward without being repeatedly pushed or pulled when inserted into the lumen of a human body, so that a surgical position can be precisely adjusted by the forward or backward movement.

BACKGROUND ART

In general, a variety of medical procedures are known in which invasive procedures are not conducted on body passages such as an esophagus (gullet) that are under or in stricture due to lesion. One of the medical procedures uses a stent made of a superelastic shape memory alloy.

Here, the medical procedure using the stent is performed by inserting the stent, in which wires made of a superelastic shape memory alloy are woven into a hollow cylindrical body having a predetermined length, into a body passage that is under or in stricture due to lesion, with a volume thereof minimized, and distending the body passage that is under or in stricture due to lesion in a radial outward direction until the volume of the stent (or a diameter of a body passage or organ) is restored to its original state.

This medical procedure using the stent requires a separate insertion instrument to insert the stent into the body passage that is under or in stricture.

In this case, the stent insertion instrument for inserting the stent is configured to insert a movable tube from the outside into an outer tube connected to an instrument body to be gripped so as to be able to move the movable tube at a trailing end of the outer tube in a forward/backward direction. Here, a leading end of the movable tube is configured to push the stent that is inserted and mounted into a leading end of the outer tube with a volume thereof reduced.

This stent insertion instrument inserts the stent, which is inserted and mounted into the leading end of the outer tube with the volume thereof reduced, into a body passage such as a blood vessel that is under or in stricture due to lesion.

Here, when the stent is inserted into the body passage that is under or in stricture due to lesion, the insertion is observed by an endoscope inserted separately.

In this way, after the stent reaches the point of stricture, the stent is pushed out of the leading end of the outer tube by an action of pushing the movable tube. While the stent is pushed out of the outer tube from the leading end thereof and is distended and restored to its original shape, the stent is installed so as to push the body passage that is under or in stricture in the radial outward direction.

However, such a conventional stent insertion instrument is not convenient, because the movable tube should be operated in the instrument body using a hand in such a way that it is pushed or pulled in a forward/backward direction in order to be accurately inserted into the targeted organ or body passage that is under or in stricture due to lesion.

Further, the conventional stent insertion instrument is configured so that a surgical position is adjusted by the pushing or pulling operation, and thus has a problem in that it is difficult to accurately select the surgical position, and that fatigue may affect the hand due to the repeated operation.

For this reason, a catheter that can accurately adjust the surgical position by easily converting rotation into reciprocation without the pushing or purling operation and reduce the occurrence of fatigue is urgently required.

DISCLOSURE

Technical Problem

Accordingly, the present invention has been made keeping in mind the above problems occurring in the related art, and is intended to provide a catheter operating structure in which a medical device is easily rotated to move forward/backward without being repeatedly pushed or pulled in order to insert the medical device.

Further, the present invention serves to provide a catheter operating structure in which a surgical position for a medical device can be accurately adjusted by forward/backward movement converted from rotation based on screwing.

In addition, the present invention serves to provide a catheter operating structure in which a position of an injection member can be separately adjusted, and thus a position of a separate injector or a separate procedure instrument can be selectively adjusted when the separate injector or the separate medical device is used.

Technical Solution

In an aspect, the present invention provides a catheter operating structure that is applied to a catheter for inserting a stent or another medical device into a human body in order to distend a blood vessel or a lumen of the human body which is undergoing stricture due to lesion. The catheter operating structure includes: a rotary member in which a spiral shaft formed on one side of a handle for rotation is inserted into one end of a tubular body; a movable member which is formed in a tube shape and in which a female spiral end is formed at one end thereof and is spirally coupled with the spiral shaft; and an injection member moving member which moves together when the movable member moves, or is unlocked to move alone in a lengthwise direction of the movable member, and in which an injection member, which passes through the movable member and the body and injects an injector or discharges air, is coupled in the front thereof. When the spiral shaft is rotated together by rotation of the handle in a state in which the spiral shaft is spirally coupled to the female spiral end, the movable member moves forward or backward in a lengthwise direction of the body without being rotated due to the injection member moving member passing through the body.

Advantageous Effects

According to the catheter operating structure as described above, a medical device is easily rotated to move forward/backward without being repeatedly pushed or pulled in order to insert the medical device.

Further, a surgical position for a medical device can be accurately adjusted by forward/backward movement converted from rotation based on screwing.

In addition, a position of an injection member can be separately adjusted, and thus a position of a separate injector or a separate procedure instrument can be selectively adjusted when the separate injector or the separate medical device is used.

DESCRIPTION OF DRAWINGS

FIG. 9 is a perspective view showing a state in which the movable member and the injection member moving member are operated by rotation of the motor when a switch is turn on.

LISTS OF SYMBOLS USED FOR MAIN PARTS OF THE DRAWINGS

10a: rotary member through-hole, 10: rotary member, 11: handle, 11a: protrusion, 12: spiral shaft, 12a: rotary end, 13: body slide hole, 14: body long slot, 15: body, 15a: fitting end, 15b: cover end through-hole, 15c: cover end, 15e: cover fastener, 15f: through-hole, 15g: fastener, 16: motor, 17: switch, 20: movable member, 21: female spiral end, 23: movable slide hole, 24: movable long slot, 25: hooking ridge, 30: injection member, 31: injection holder, 40: injection member moving member, 41: pressable button, 42: moving member body, 42a: wings, 43: hooking piece, 50: guide wire, 100: catheter, B: battery

BEST MODE

The present invention is intended to provide a catheter operating structure in which a medical device such as a stent is rotated to move forward or backward without being repeatedly pushed or pulled when inserted into the lumen of a human body, so that a surgical position can be precisely adjusted by the forward or backward movement.

MODE FOR INVENTION

Hereinbelow, exemplary embodiments of the present invention will be described in detail with reference to the accompanying drawings.

Figure 1:
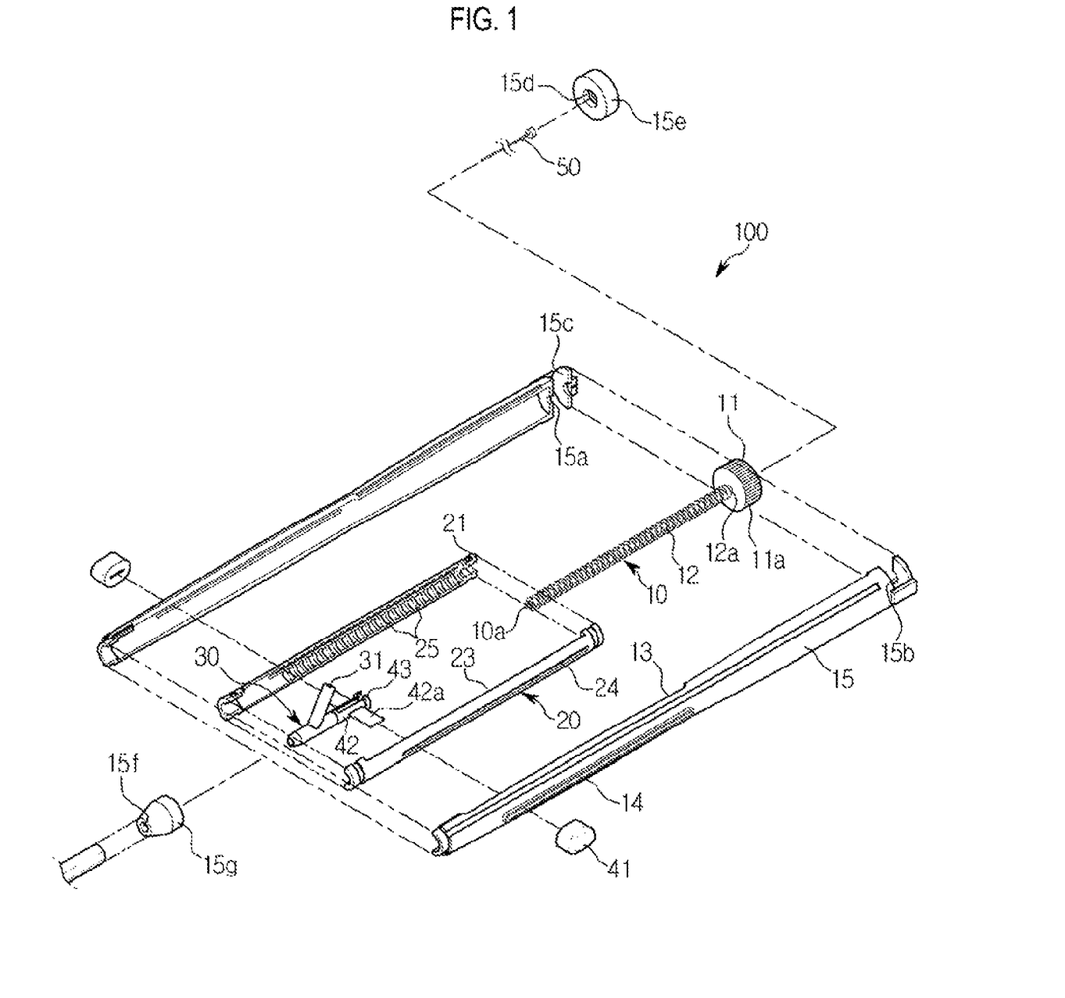
FIG. 1 is a disassembled perspective view of a catheter operating structure according to the present invention.
Figure 2A:
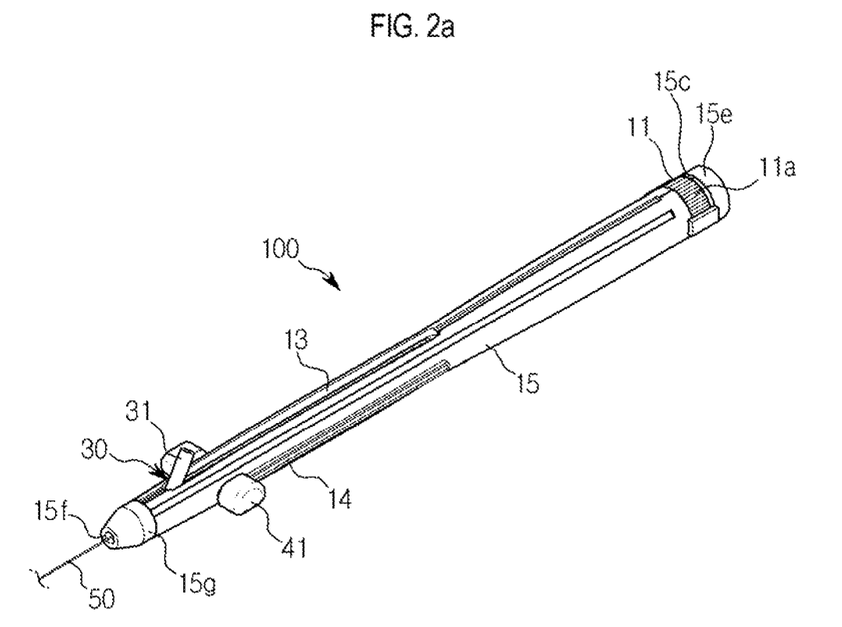
FIG. 2a is an assembled perspective view of the catheter operating structure according to the present invention.

As shown in FIGS. 1 and 2a, a catheter operating structure according to an embodiment of the present invention is applied to a catheter 100 for inserting a stent or another medical device into a human body in order to distend a blood vessel or a lumen of the human body which undergoes stricture due to lesion, and includes a rotary member 10 in which a spiral shaft 12 inserted into a tubular body 15 is formed, a movable member 20 in which a female spiral end 21 is formed and spirally coupled to the spiral shaft 12, and an injection member moving member 40 which is inserted into the movable member 20 and to which an injection member 30 is coupled in the front thereof.

First, the rotary member 10 is configured so that the spiral shaft 12 extending from one side of a handle 11 for rotation is inserted through one end of the tubular body 15.

Here, the handle 11 is formed in a wheel shape and is provided with protrusions 11a on an outer circumferential surface thereof so as to prevent sliding. The spiral shaft 12 is formed so as to have a smaller diameter than the handle 11, and is provided with a cylindrical rotary end 12a at a portion at which it is connected to the handle 11.

Moreover, the rotary member 10 is provided with a rotary member through-hole 10a passing through the handle 11 and the spiral shaft 12.

Meanwhile, the body 15 is bisected in a lengthwise direction, and is coupled so as to be able to be assembled and disassembled. In a coupled state, the body 15 is provided with a body slide hole 13. The body 15 is provided with body long slots 14 on radial opposite sides thereof.

That is, the body slide hole 13 is one in number, and the body long slots 14 are formed in a pair at positions orthogonal to the body slide hole 13.

Furthermore, the rotary end 12a of the spiral shaft 12 is fitted into one end of the body 15 and is slidably rotated when the handle 11 is rotated. To this end, the body 15 is provided with a fitting end 15a at one end thereof.

Further, the body 15 is provided with a cover end 15c outside the fitting end 15a. A cover end through-hole 15b is formed between the cover end 15c and the fitting end 15a so as to expose the outer circumferential surface of the handle 11 and to cover the other end of the handle 11.

Further, when the body 15 is assembled in a bisected state, a cover fastener 15e is fastened to the rear of the cover end 15c. To this end, the cover fastener 15e is provided with a fastening hole 15d in the center of a front end thereof. A front end of the body 15 is fitted into a fastener 15g, through the center of which a through-hole 15f passes. Thereby, the body 15 is prevented from being disassembled.

Meanwhile, the movable member 20 is formed in a shape of a pipe, at one end of which the female spiral end 21 is formed, and is configured so that the spiral shaft 12 is spirally coupled to the female spiral end 21.

The movable member 20 is bisected in a lengthwise direction, and is coupled in an assemblable or disassemblable structure like the body 15. In an assembled state, the movable member 20 is provided with a movable slide hole 23 matched with the body slide hole 13. The movable member 20 is provided with movable long slots 24 matched with the body long slots 14 on radial opposite sides thereof.

Further, the movable member 20 is provided with a plurality of hooking ridges 25 protruding inward from an inner circumferential surface thereof at regular intervals in a lengthwise direction thereof.

In addition, the injection member moving member 40 moves together when the movable member 20 moves, or is unlocked to move alone in the lengthwise direction of the movable member 20. The injection member 30, which passes through the movable member 20 and the body 15 and injects an injector or discharges air, is coupled in the front of the injection member moving member 40.

Here, one end of a moving member body 42 to which pressable buttons 41 of the injection member moving member 40 are coupled is partly cut and bisected. The bisected end of the moving member body 42 is provided with a hooking piece 43 hooked on one of the hooking ridges 25.

In this case, the moving member body 42 is coupled with the injection member 30 before the movable member 20 is assembled. The pressable buttons 41 are assembled to a pair of wings 42a protruding outward from the moving member body 42.

Figure 2B:
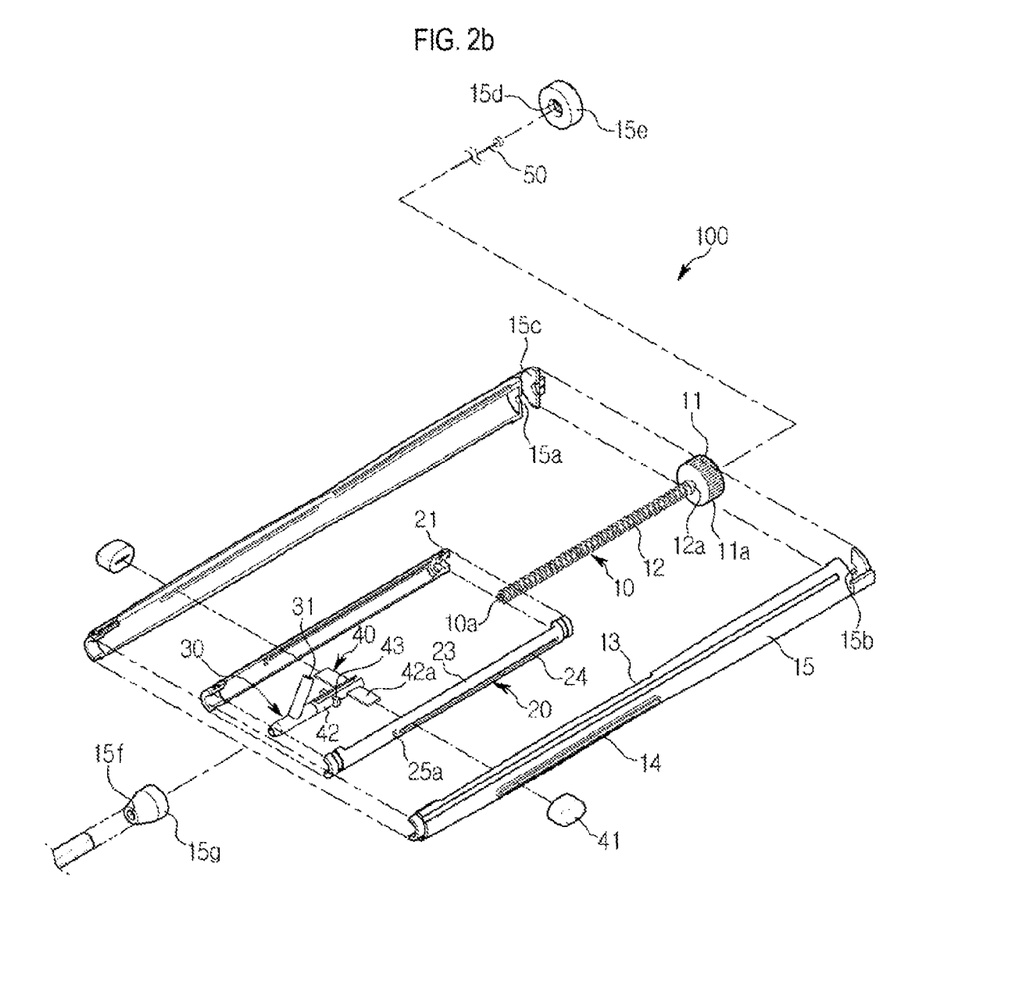
FIG. 2b is a disassembled perspective view according to another embodiment of a movable member.
Figure 2C:
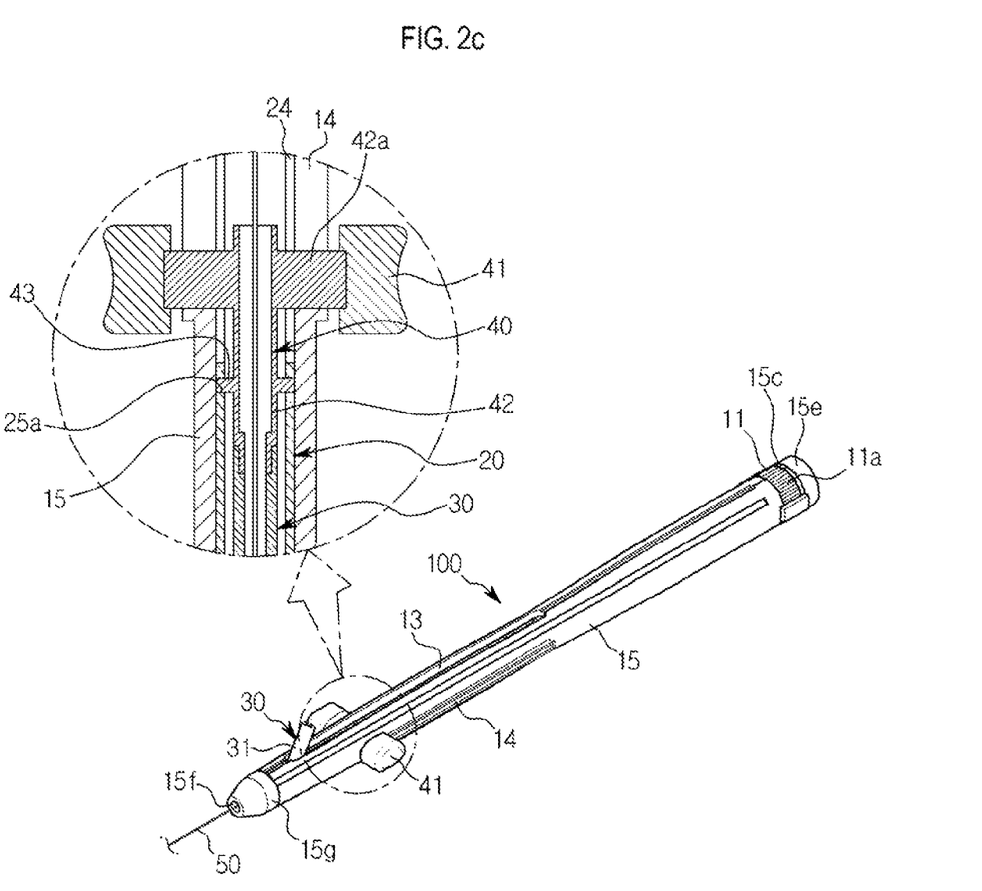
FIG. 2c is an assembled perspective view of FIG. 2b along with a partial cross-sectional view.

As shown in FIGS. 2b and 2c, as another example, the movable member 20 may be provided with hooking holes 25a in a front portion thereof.

In detail, in a state in which the injection member moving member 40 is inserted into the movable member 20 and hooking pieces 43 are inserted into the hooking holes 25a, when the pressable buttons 41 are pressed, the hooking pieces 43 are released from the hooking holes 25a, and then the injection member moving member 40 slides in a forward or backward direction.

Here, the hooking pieces 43 are formed in front of the wings 42a formed on the moving member body 42 in one body.

Figure 3:
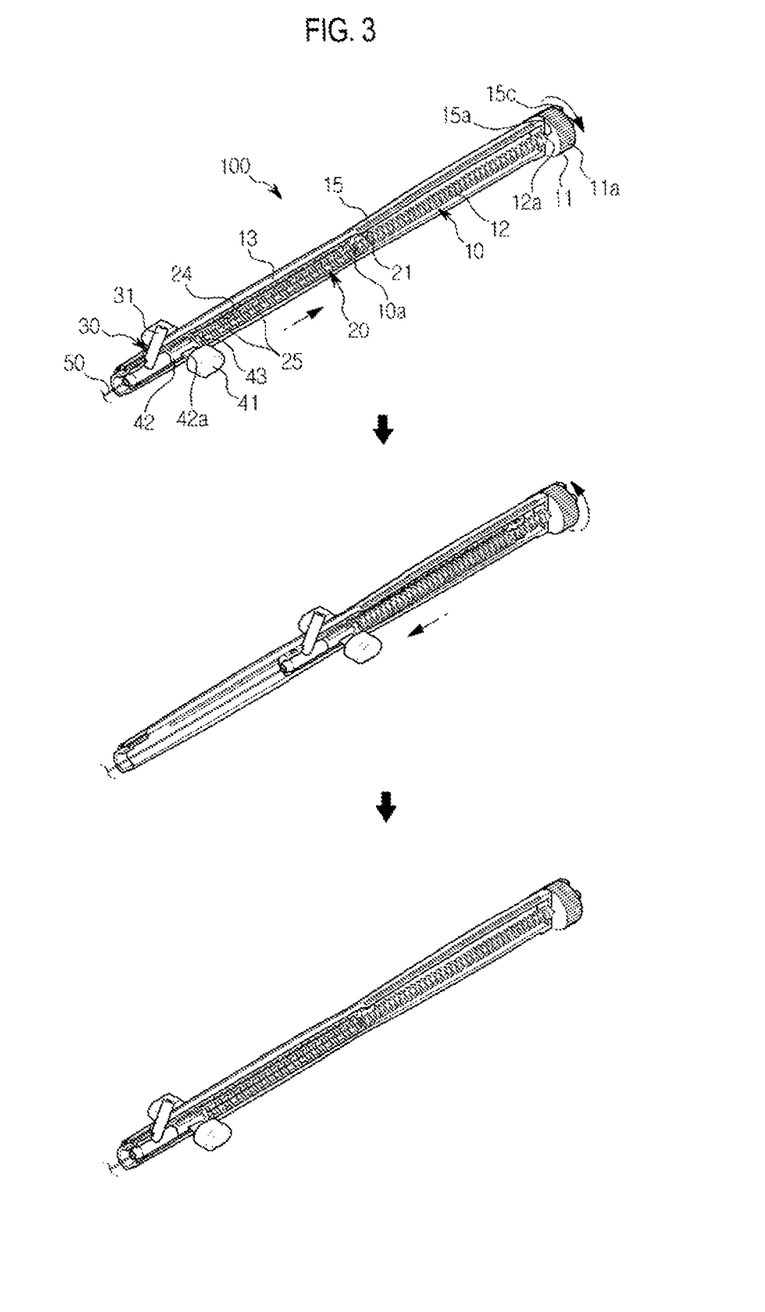
FIG. 3 is a perspective view showing a state in which a movable member and an injection member moving member are operated when a handle of a rotary member according to the present invention is rotated.

As shown in FIG. 3, in a state in which the spiral shaft 12 is spirally coupled to the female spiral end 21 of the movable member 20, when the spiral shaft 12 is rotated by the rotation of the handle 11, the movable member 20 moves forward or backward in the lengthwise direction of the body 15 without being rotated due to the injection member moving member 40 passing through the body 15.

In this case, a guide wire 50 inserted into a human body passes through the rotary member through-hole 10a of the rotary member 10, the cover end through-hole 15b of the cover end 15c, and the through-hole 15f of the fastener 15g.

Figure 7:
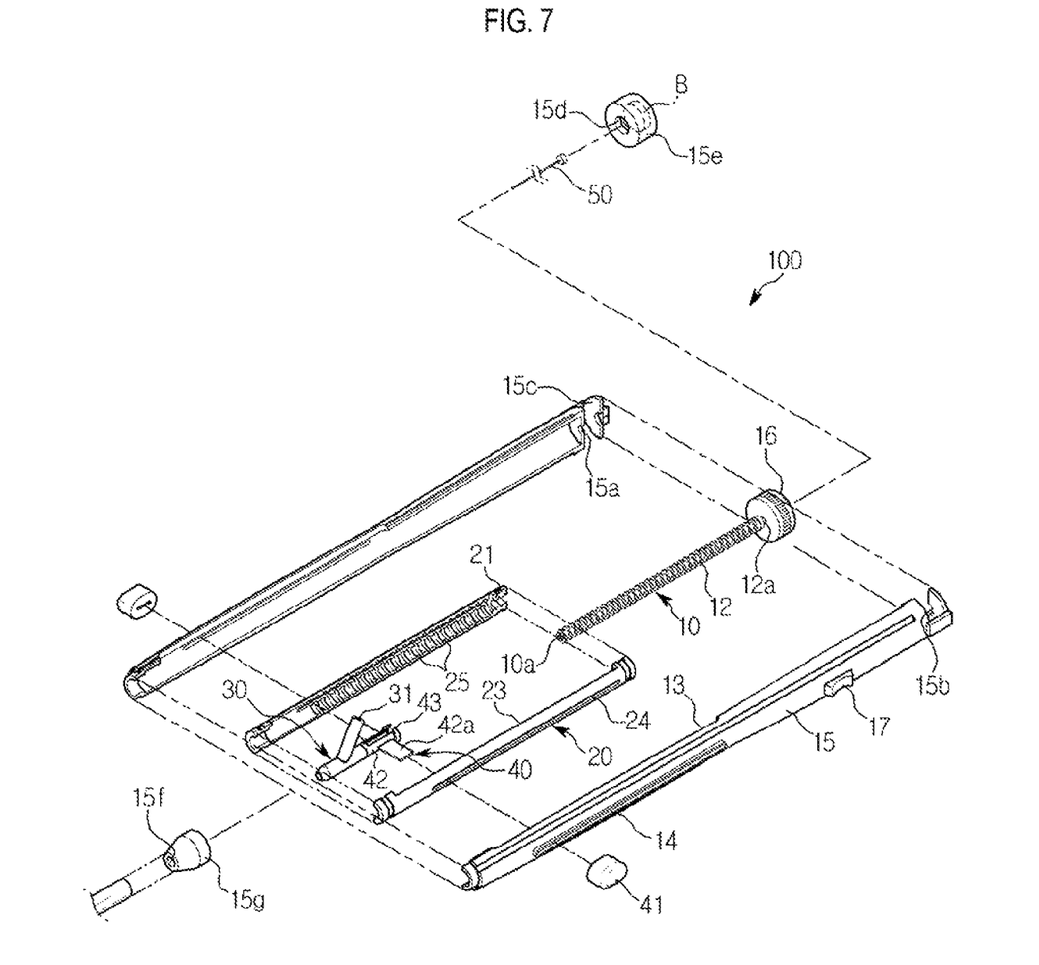
FIG. 7 is a disassembled perspective view configured so that the rotary member is rotated using a motor.
Figure 8:
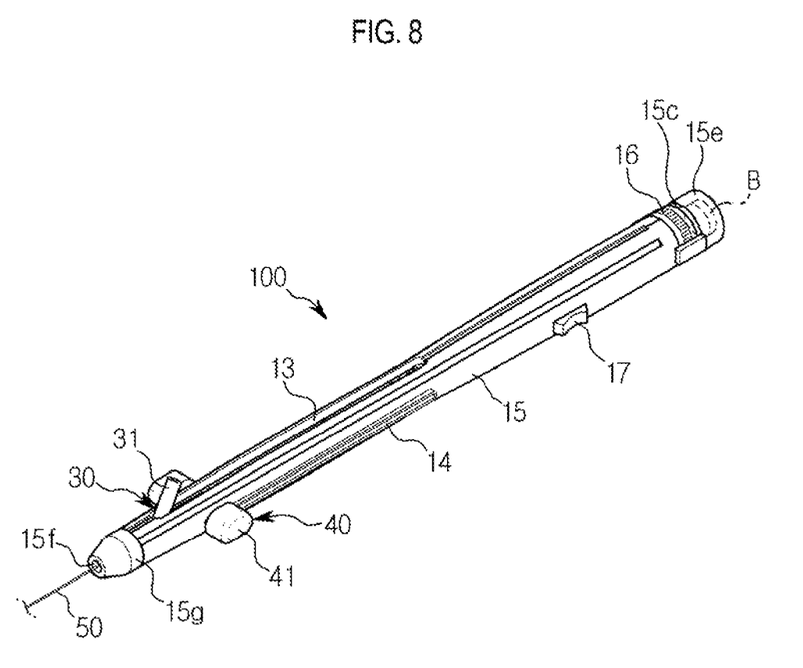
FIG. 8 is an assembled perspective view configured so that the rotary member is rotated using the motor.
Figure 9:
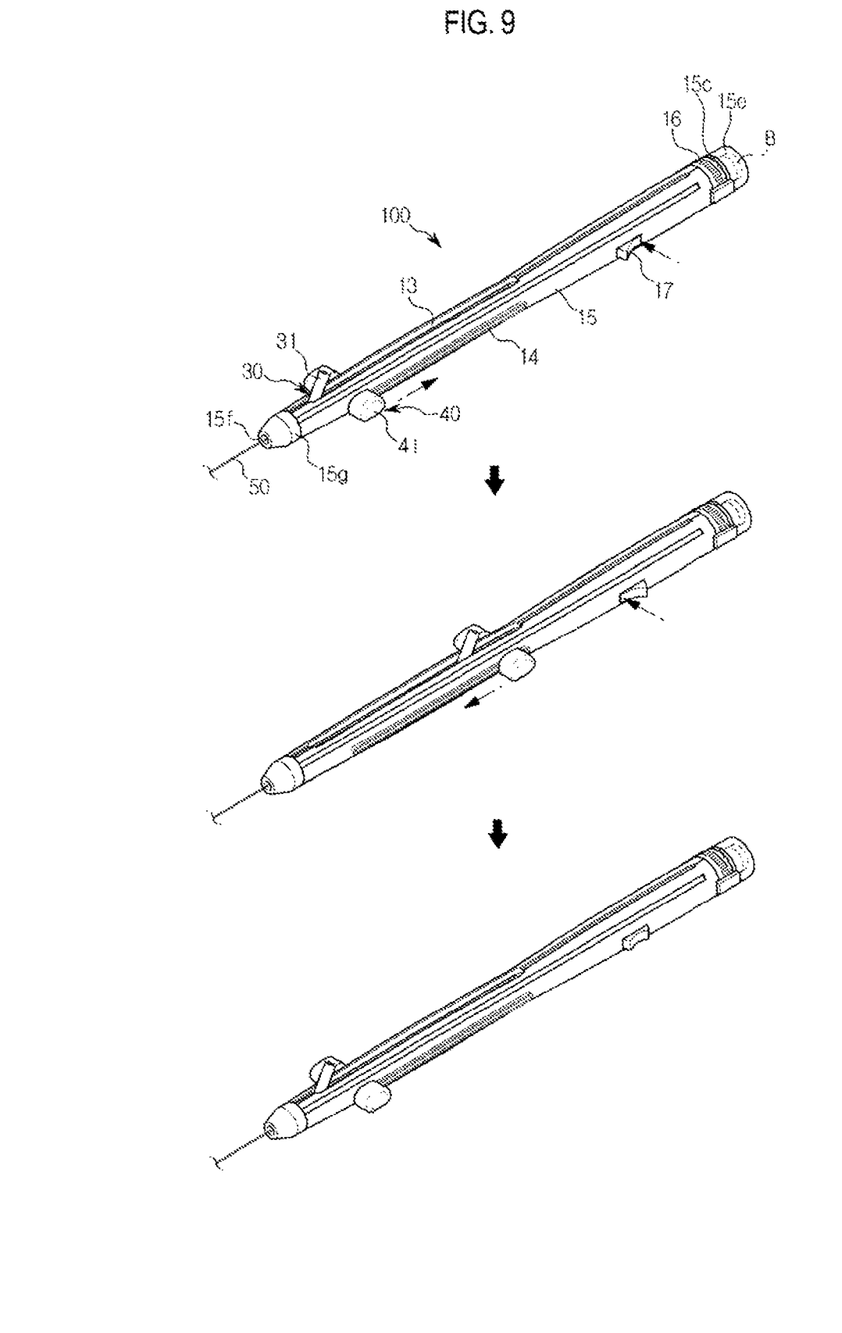

As shown in FIGS. 7 to 9, a catheter operating structure according to another embodiment of the present invention is applied to a catheter 100 for inserting a stent or another medical device into a human body in order to distend a blood vessel or a lumen of the human body which undergoes stricture due to lesion, and includes a rotary member 10 in which a spiral shaft 12 is coupled so as to foe rotated by a motor 16 rotating in a forward or backward direction. The spiral shaft 12 is inserted into one end of a tubular body 15 on which a switch 17 controlling an operation of the motor 16 is installed in an exposed state.

Further, when the body 15 is assembled in a bisected state, a cover fastener 15e is fastened to the rear of the cover end 15c. To this end, the cover fastener 15e is provided with a fastening hole 15d in the center of a front end thereof. A front end of the body 15 is fitted into a fastener 15g, through the center of which a through-hole 15f passes. Thereby, the body 15 is prevented from being disassembled.

Here, a battery B is inserted into the cover fastener 15e and is in contact with the motor 16 so as to be able to transmit power.

The switch 17 is configured to pivot about the center thereof. In detail, when opposite ends of the switch 17 are pressed, the rotational directions of the motor 16 are switched. When the pressing of the switch 17 is released, the switch 17 is restored to its original state.

Furthermore, the switch 17 is configured to be restored when the pressing thereof is released. To this end, an elastic member such as a coil spring or a leaf spring for the restoration is mounted in the opposite ends of the switch 17. When the switch 17 is maintained in a horizontal state, the motor 16 is not driven. When each of the opposite ends of the switch 17 is pressed, a closed contact is formed between the battery and the motor 17 so that the motor 16 is rotated in the forward or backward direction.

That is, when the motor 16 is rotated in the forward or backward direction by pressing the switch 17, the spiral shaft 12 is rotated in the state in which it is spirally coupled to the female spiral end 21, and the movable member 20 moves forward or backward in the lengthwise direction of the body 15 without being rotated due to the injection member moving member 40 passing through the body 15.

Meanwhile, the guide wire 50 may be inserted and fixed in the spiral shaft 12 without passing through the motor 16, or in the injection member 30 or the injection member moving member 40.

An operation of the catheter operating structure configured as described above will be described as follows.

As shown in FIGS. 1 and 2a, as fox a sequence in which the catheter 100 is assembled, the injection member 30 is coupled to the moving member body 42 constituting the injection member moving member 40, and then is inserted into the bisected movable member 20. Thereby, the movable member 20 is assembled.

Here, an injection holder 31 of the injection member 30 is exposed through the movable slide hole 23 of the movable member 20, and the wings 42a formed on the moving member body 42 are exposed through the movable long slots 24 at the radial opposite sides.

The injection holder 31 functions to inject a medicament into a human body using a separate procedure instrument such as an injector when a medical procedure is conducted, or discharge air in the human body to the outside.

The hooking pieces 43 formed on one end of the moving member body 42 are kept hooked on one of the hooking ridges 25 of the movable member 20.

Afterwards, the rotary end 12a of the spiral shaft 12 of the rotary member 10 is spirally coupled to the female spiral end 21 of the movable member 20. In this state, the rotary end 12a of the spiral shaft 12 is fitted into the fitting end 15a formed at the half cover end 15c of the bisected body 15. Thereby, the bisected body 15 is assembled.

Here, the injection holder 31 of the injection member 30 passes through the body slide hole 13 via the movable slide hole 23 of the movable member 20 in an exposed state, and the wings 42a formed on the moving member body 42 are exposed through the body long slots 14 via the movable long slots 24 at the radial opposite sides.

Next, the cover fastener 15e is fastened to an upper portion of the cover end 15c of the body 15, and the fastener 15g is fitted into one end of the body 15 to which the cover fastener 15e is coupled. The pressable buttons 41 are fitted into the wings 42a.

In this way, to use the assembled catheter 100 when a medical device such as a stent is inserted into a human body, the guide wire 50 sequentially passes through the rotary member through-hole 10a of the rotary member 10, the cover end through-hole 15b of the cover end 15c, and the through-hole 15f of the fastener 15g, and is inserted into the human body.

Here, in a state in which a tube (whose reference numeral is not shown) into which the medical device is inserted in front of the fastener 15g coupled to the other end of the body 15 is coupled, the medical device is inserted into the human body to be inserted.

Figure 4:
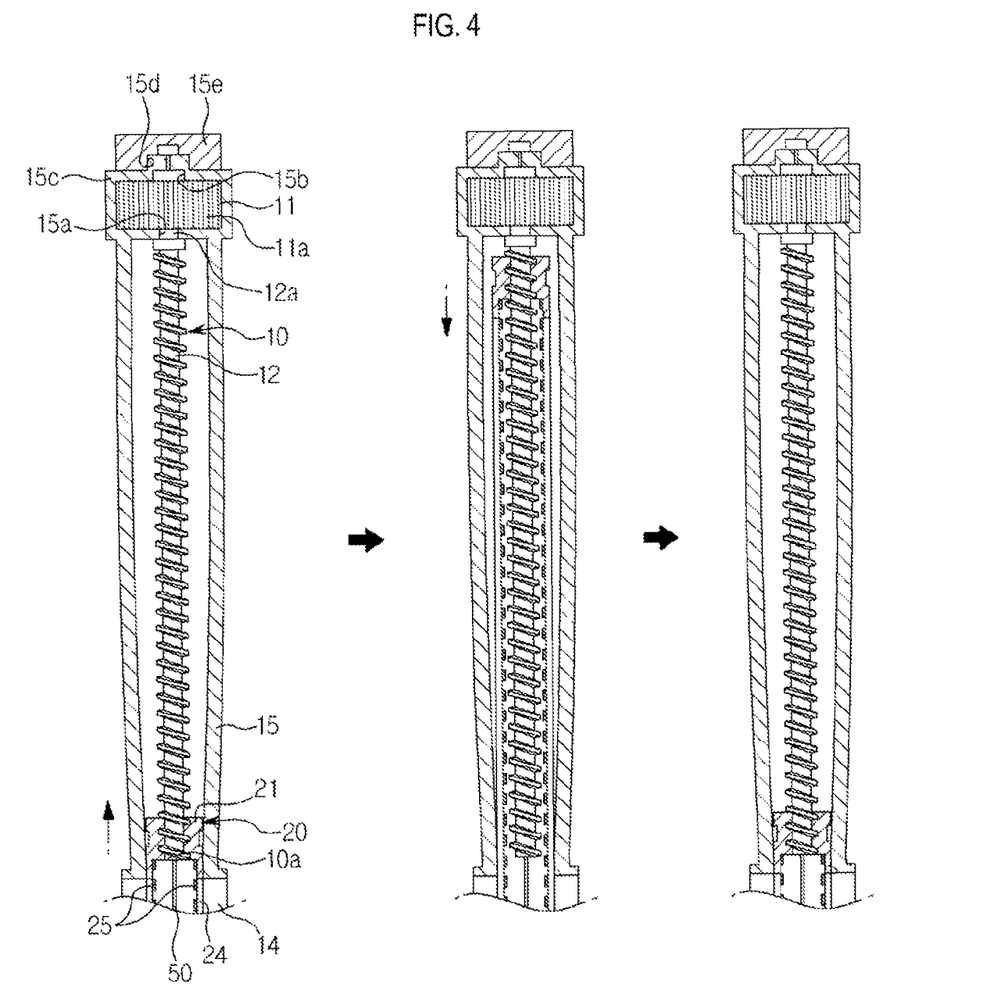
FIG. 4 is a cross-sectional view showing a state in which the movable member is operated when the handle of the rotary member according to the present invention is rotated.

As shown in FIGS. 3 and 4, when the medical device approaches a position to be inserted, the handle 11 of the rotary member 10 is rotated in a clockwise or counterclockwise direction, and the spiral shaft 12 is rotated at the fitting end 15a of the cover end 15c into which the rotary end 12a thereof is fitted. Then, the movable member 20, to the female spiral end 21 of which the spiral shaft 12 is spirally coupled, moves forward or backward.

Here, as the spiral shaft 12 rotates, the movable member 20 is not rotated together. This is because the wings 42a of the moving member body 42 sequentially passes through the movable long slots 24 of the movable member 20 and the body long slots 14 in an exposed state, and are supported there. The rotation of the spiral shaft 12 is converted into the reciprocation, and thereby the movable member 20 moves forward or backward.

Figure 5:
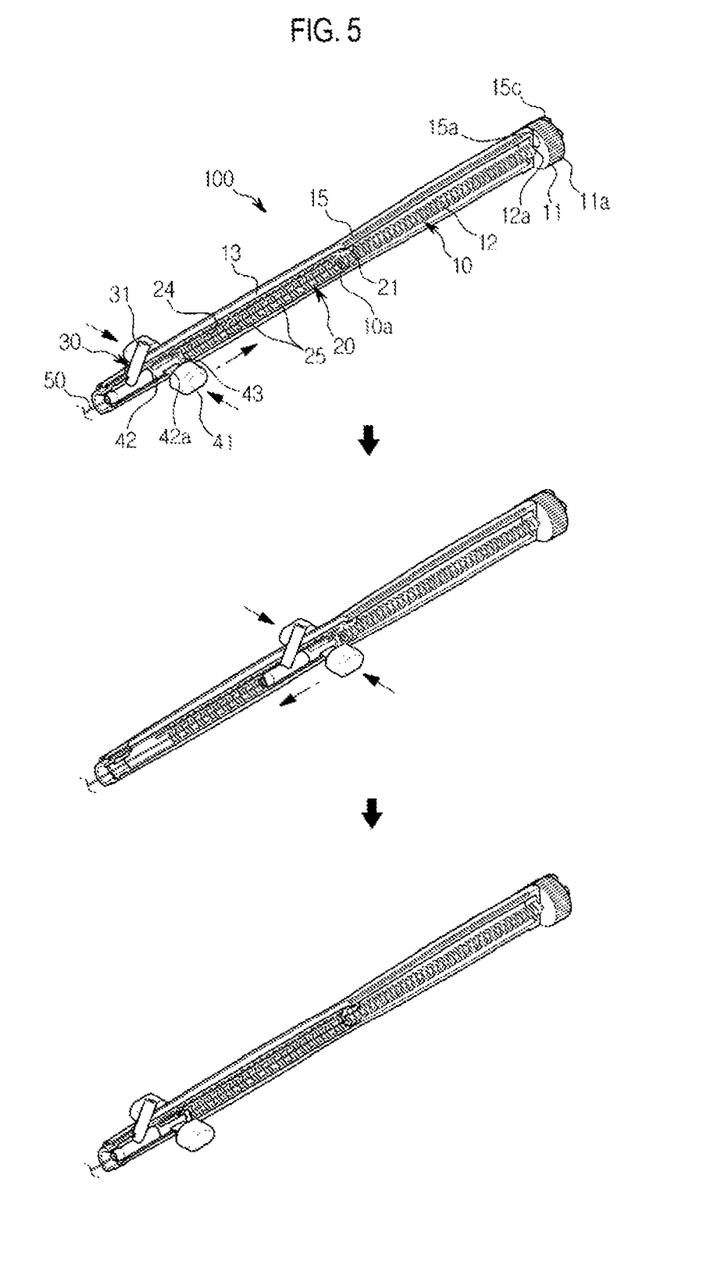
FIG. 5 is a perspective view showing a state in which pressable buttons of the injection member moving member according to the present invention are pressed so as to move the movable member.
Figure 6:
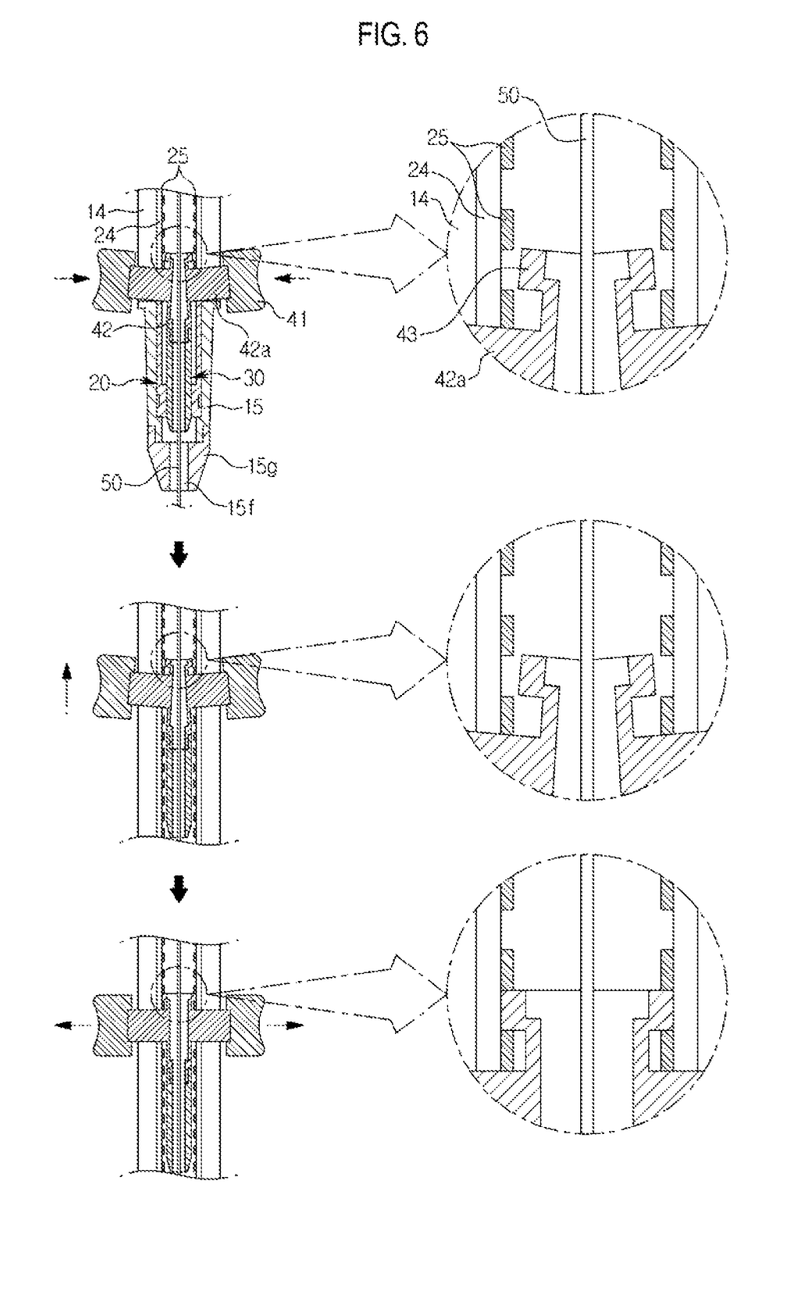
FIG. 6 is a partial cross-sectional view showing a case in which the pressable buttons are separated from hooking ridges of the movable member so as to be movable when the pressable buttons of the injection member moving member according to the present invention are pressed.

As shown in FIGS. 5 and 6, the injection member moving member 40 moves the injection member 30 when the position of the injection member 30 is adjusted. To move the injection member 30, when the pressable buttons 41 are pressed, the bisected parts of the moving member body 42 are pressed so as to approach each other. The hooking pieces 43 hooked on one of the hooking ridges 25 are released. In this state, the injection member moving member 40 is manually moved forward or backward.

Then, when the movement of the injection member moving member 40 is completed, the pressing of the pressable buttons 41 is released. Thereby, the moving member body 42 is restored in a radial outward direction by its elastic force, and thus the hooking pieces 43 are hooked on one of the hooking ridges 25. As a result, the position of the injection member moving member 40 is fixed.

Consequently, the medical device is rotated without being repeatedly pushed or pulled. Thereby, a surgical position for the medical device can be precisely adjusted. Also, work required to perform the adjustment is easy, and a degree of fatigue of the hand of an operator can be remarkably reduced.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A catheter operating structure that is applied to a catheter for inserting a stent or another medical device into a human body in order to distend a blood vessel or a lumen of the human body which is undergoing stricture due to lesion, the catheter operating structure comprising:
   a rotary member in which a spiral shaft formed on one side of a handle for rotation is inserted into one end of a tubular body;
   a movable member which is formed in a tube shape and in which a female spiral end is formed at one end thereof and is spirally coupled with the spiral shaft; and
   an injection member moving member which moves together when the movable member moves, or is unlocked to move alone in a lengthwise direction of the movable member, and in which an injection member, which passes through the movable member and the tubular body and injects an injector or discharges air, is coupled in the front thereof,
   wherein, when the spiral shaft is rotated together by rotation of the handle in a state in which the spiral shaft is spirally coupled to the female spiral end, the movable member moves forward or backward in a lengthwise direction of the tubular body without being rotated due to the injection member moving member passing through the tubular body, and wherein the tubular body includes body long slots formed on radial opposite sides thereof so that the injection member moving member moves slidably;
   the movable member includes movable long slots that are formed on radial opposite sides thereof and are matched with the body lone slots; and
   the injection member moving member includes a pair of pressable buttons that are formed on radial opposite sides thereof and move slidably in a state in which the pressable buttons are exposed through the body long slots and the movable long slots.

2. The catheter operating structure according to claim 1, wherein:
   the tubular body includes a body slide hole formed in the lengthwise direction thereof so that the movable member or the injection member moving member moves in a state in which an injection holder formed on the injection member is exposed; and
   the movable member include a movable slide hole matched with the body slide hole so that the injection member moving member moves in the state in which the injection holder is exposed.

3. The catheter operating structure according to claim 1, wherein:
   the movable member includes a plurality of hooking ridges protruding inward from an inner circumferential surface thereof at regular intervals in a lengthwise direction thereof; and
   when the pressable buttons are pressed after the injection member moving member is inserted into the movable member, hooking is released from the hooking ridges, whereas when the pressing of the pressable buttons is released, the hooking on the hooking ridges takes place.

4. The catheter operating structure according to claim 3, wherein:
   one end of the moving member body to which the pressable buttons of the injection member moving member are coupled is partly cut and bisected; and
   the bisected end of the moving member body includes hooking pieces hooked on the hooking ridges of the movable member.

5. The catheter operating structure according to claim 4, wherein:
   the movable member includes hooking holes formed in a front portion thereof; and
   in a state in which the injection member moving member is inserted into the movable member and the hooking pieces are inserted into the hooking holes, when the pressable buttons are pressed, the hooking pieces are released from the hooking holes, and then the injection member moving member slides in a forward or backward direction.

6. A catheter operating structure that is applied to a catheter for inserting a stent or another medical device into a human body in order to distend a blood vessel or a lumen of the human body which is undergoing stricture due to lesion, the catheter operating structure comprising:
   a rotary member in which a spiral shaft coupled so as to be rotated by driving of a motor rotating in a forward or backward direction is inserted into one end of a tubular body from which a switch controlling an operation of the motor is exposed;
   a movable member which is formed in a tube shape and in which a female spiral end is formed at one end thereof and is spirally coupled with the spiral shaft; and
   an injection member moving member which moves together when the movable member moves, or is unlocked to move alone in a lengthwise direction of the movable member, and in which an injection member, which passes through the movable member and the tubular body and injects an injector or discharges air, is coupled in the front thereof, wherein, when the motor is rotated in the forward or backward direction by turning on the switch, the spiral shaft is rotated in a state in which the spiral shaft is spirally coupled to the female spiral end, and the movable member moves forward or backward in a lengthwise direction of the tubular body without being rotated due to the injection member moving member passing through the tubular body, and wherein the tubular body includes body lone slots formed on radial opposite sides thereof so that the injection member moving member moves slidably;

the movable member includes movable long slots that are formed on radial opposite sides thereat and are matched with the body long slots; and the injection member moving member includes a air of pressable buttons that are formed on radial opposite sides thereof and move slidably in a state in which the pressable buttons are exposed through the body lone slots and the movable long slots.

7. The catheter operating structure according to claim 6, wherein the switch is configured to pivot about the center thereof in such a way that, when opposite ends of the switch are pressed, the rotational directions of the motor are switched, and that when the pressing of the switch is released, the switch is restored to an original state.

\* \* \* \* \*